(12) United States Patent
Carlson et al.

(10) Patent No.: US 8,998,974 B2
(45) Date of Patent: Apr. 7, 2015

(54) WOVEN FABRIC WITH CARBON NANOTUBE STRANDS

(75) Inventors: James M. Carlson, Bloomington, IN (US); Shyam S. V. Kuppurathanam, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1259 days.

(21) Appl. No.: 12/242,246

(22) Filed: Sep. 30, 2008

(65) Prior Publication Data

US 2009/0171440 A1    Jul. 2, 2009

Related U.S. Application Data

(60) Provisional application No. 61/014,236, filed on Dec. 17, 2007.

(51) Int. Cl.
*A61F 2/06* (2013.01)
*D03D 15/00* (2006.01)
*A61F 2/07* (2013.01)
*D03D 1/00* (2006.01)
*D03D 3/02* (2006.01)
*D03D 13/00* (2006.01)
*D03D 15/02* (2006.01)
*A61F 2/00* (2006.01)
*A61F 2/89* (2013.01)

(52) U.S. Cl.
CPC *D03D 15/00* (2013.01); *A61F 2/06* (2013.01); *A61F 2/07* (2013.01); *A61F 2002/0068* (2013.01); *A61F 2002/065* (2013.01); *D03D 1/0041* (2013.01); *D03D 3/02* (2013.01); *D03D 13/008* (2013.01); *D03D 15/0061* (2013.01); *D03D 15/02* (2013.01); *D10B 2101/12* (2013.01); *D10B 2101/20* (2013.01); *D10B 2321/021* (2013.01); *D10B 2321/022* (2013.01); *D10B 2321/042* (2013.01); *D10B 2321/10* (2013.01); *D10B 2331/021* (2013.01); *D10B 2331/04* (2013.01); *D10B 2331/10* (2013.01); *D10B 2401/046* (2013.01); *D10B 2401/061* (2013.01); *D10B 2401/063* (2013.01); *D10B 2509/06* (2013.01); *A61F 2/89* (2013.01)

(58) Field of Classification Search
USPC ......... 623/1.15, 1.49, 1.51; 606/151; 442/194
See application file for complete search history.

(56) References Cited

U.S. PATENT DOCUMENTS

| | | | |
|---|---|---|---|
| 5,741,325 A | 4/1998 | Chaikof et al. | |
| 7,144,422 B1 | 12/2006 | Rao | |
| 7,247,290 B2 | 7/2007 | Lobovsky et al. | 423/447.1 |
| 2003/0065355 A1 | 4/2003 | Weber | |
| 2005/0038498 A1 | 2/2005 | Dubrow et al. | |

(Continued)

OTHER PUBLICATIONS

Zheng, Lianxi et al., "Carbon-Nanotube Cotton for Large-Scale Fibers," *Adv. Mater.* 19 (2007) pp. 2567-2570.

*Primary Examiner* — Thomas J Sweet
*Assistant Examiner* — Matthew Schall
(74) *Attorney, Agent, or Firm* — Brinks Gilson & Lione

(57) ABSTRACT

A woven fabric for an implantable medical device includes a plurality of carbon nanotube strands interwoven with a plurality of textile strands, where each carbon nanotube strand comprises a plurality of carbon nanotubes. An implantable medical device comprises a component and a fabric secured to the component, where the fabric includes a plurality of woven carbon nanotube strands, and each of the carbon nanotube strands comprises a plurality of carbon nanotubes.

18 Claims, 6 Drawing Sheets

(56) References Cited

U.S. PATENT DOCUMENTS

| | | |
|---|---|---|
| 2005/0075727 A1 | 4/2005 | Wheatley |
| 2006/0052865 A1 | 3/2006 | Banas |
| 2006/0100696 A1 | 5/2006 | Atanasoska et al. |
| 2006/0129234 A1 | 6/2006 | Phaneuf et al. |
| 2006/0136042 A1 | 6/2006 | Holman et al. |
| 2006/0173397 A1 | 8/2006 | Tu et al. |
| 2006/0190074 A1 | 8/2006 | Hill et al. |
| 2006/0204738 A1 | 9/2006 | Dubrow et al. |
| 2006/0287709 A1 | 12/2006 | Rao |
| 2006/0293743 A1 | 12/2006 | Andersen et al. |
| 2007/0043428 A1 | 2/2007 | Jennings et al. |
| 2007/0043434 A1 | 2/2007 | Meerkin et al. |
| 2007/0116631 A1 | 5/2007 | Li et al. .................. 423/447.3 |
| 2007/0212290 A1 | 9/2007 | Zheng et al. .............. 423/445 B |
| 2009/0130162 A2* | 5/2009 | Pathak et al. ................ 424/423 |
| 2009/0143227 A1* | 6/2009 | Dubrow et al. .............. 502/406 |

* cited by examiner

WOVEN FABRIC WITH CARBON NANOTUBE STRANDS

RELATED APPLICATIONS

The present patent document claims the benefit of the filing date under 35 U.S.C. §119(e) of U.S. Provisional Patent Application Ser. No. 61/014,236, filed Dec. 17, 2007, which is hereby incorporated by reference in its entirety.

TECHNICAL FIELD

The present disclosure relates to woven fabrics. More particularly, the present disclosure relates to woven fabrics for implantable medical devices.

BACKGROUND

Aneurysms occur in blood vessels at sites where, due to age, disease or genetic predisposition, the strength or resilience of the vessel wall is insufficient to prevent ballooning or stretching of the wall as blood flows therethrough. If the aneurysm is left untreated, the blood vessel wall may expand to a point at which rupture occurs, often leading to death.

To prevent rupturing of an aneurysm, such as an abdominal aortic aneurysm, a stent graft may be introduced into a blood vessel percutaneously and deployed to span the aneurysmal sac. The outer surface of each end of the stent graft is preferably sealed against the interior wall of the blood vessel at a site where the interior wall has not suffered a loss of strength or resilience. Blood flowing through the vessel is channeled through the hollow interior of the stent graft to reduce, if not eliminate, the stress on the vessel wall at the location of the aneurysmal sac. Therefore, the risk of rupture of the blood vessel wall at the aneurysmal location is significantly reduced or eliminated, and blood can pass through the vessel without interruption.

Stent grafts include a graft fabric secured to a stent. The graft is typically inserted into or pulled over the stent and sewn to its structural components. Alternatively, the stent may be formed on the graft such that the individual wires of the stent are threaded through specially provided projecting fabric loops on the surface of the graft. The stent provides rigidity and structure to hold the graft open in a tubular configuration as well as the outward radial force needed to create a seal between the graft and the vessel wall. The graft provides the tubular channel for blood flow past the aneurysm and prevents blood from pressurizing the aneurysmal sac.

SUMMARY

Described herein is a woven fabric for use in implantable medical devices. The woven fabric comprises a plurality of carbon nanotube strands interwoven with a plurality of textile strands. Each of the carbon nanotube strands comprises a plurality of carbon nanotubes.

Also described is an implantable medical device including such a woven fabric. The implantable medical device comprises a component and a fabric secured to the component. The fabric includes a plurality of woven carbon nanotube strands, where each of the carbon nanotube strands comprises a plurality of carbon nanotubes.

An advantage of a preferred embodiment of the implantable medical device is better packability into lower profile delivery systems than existing devices. Preferably, the woven fabric including the plurality of carbon nanotube strands has a reduced thickness compared to conventional fabrics without sacrificing strength or wear resistance. Another advantage of a preferred embodiment of the woven fabric is drug eluting capabilities.

DETAILED DESCRIPTION

Definitions

Figure 1:
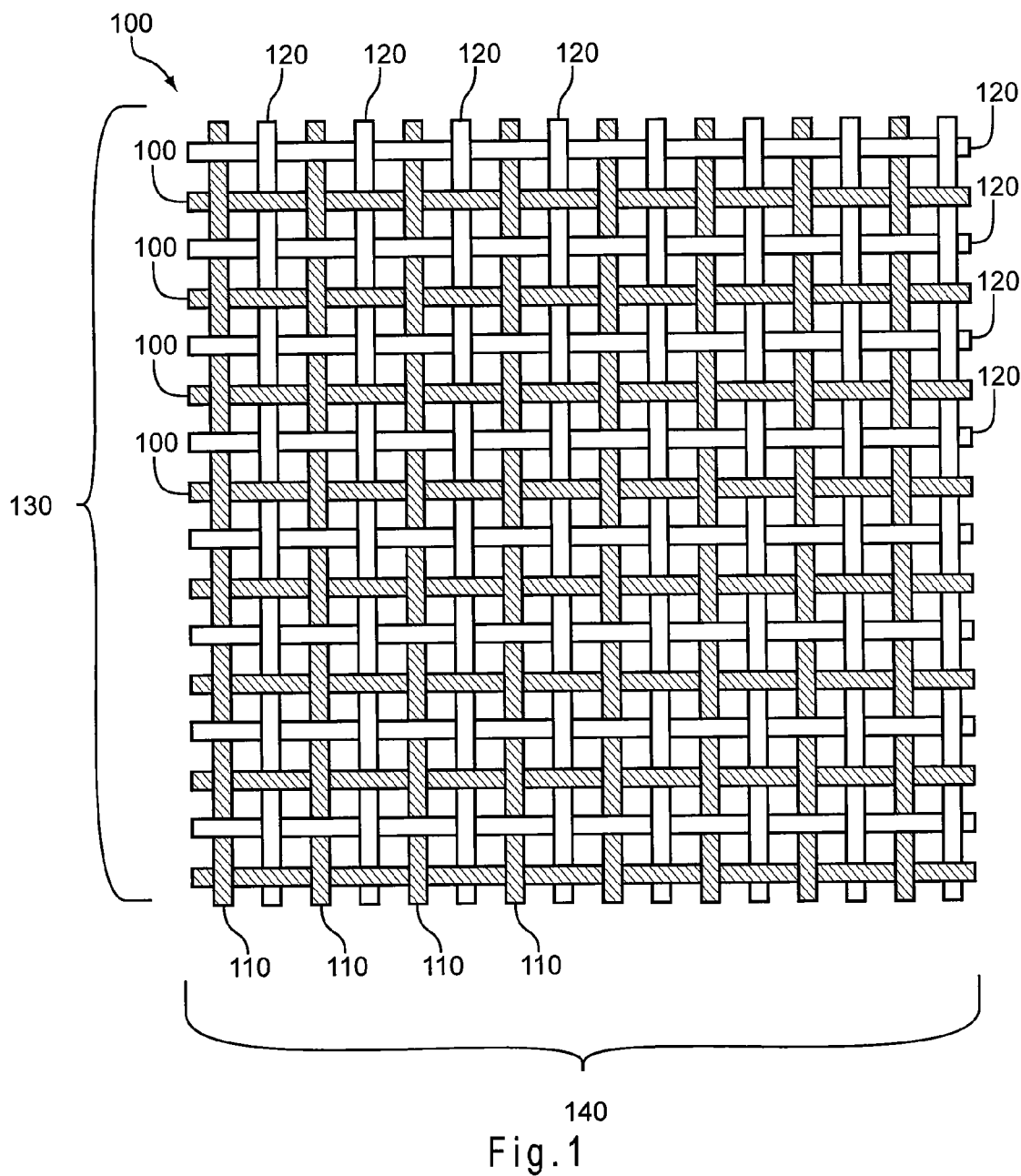
FIG. 1 is a schematic of a portion of woven fabric including carbon nanotube strands and textile strands, according to one embodiment.

The term "implantable medical device" refers to a medical device that is either permanently or temporarily inserted into a patient's body for treatment of a medical condition.

The term "strand" refers to a monofilament (e.g., a thread) or to a plurality of filaments (e.g., a yarn), with or without twist, which is suitable for weaving, knitting, or otherwise interlacing to form a fabric.

The term "denier" refers to the mass in grams of 9000 meters of a strand.

The term "ends per inch" refers to the number of warp strands in an inch. The warp strands are aligned in a "warp direction" and held taut by the loom.

The term "picks per inch" refers to the number of weft strands in an inch. The weft strands are manipulated through the warp strands in a "weft direction" to make a fabric.

Described herein is a woven fabric for an implantable medical device. The woven fabric comprises a plurality of carbon nanotube strands interwoven with a plurality of textile strands. Each of the carbon nanotube strands comprises a plurality of carbon nanotubes.

A carbon nanotube is a cylindrical arrangement of carbon atoms generally having the form of a sheet of graphite that has been rolled into a cylinder. Carbon nanotubes were first discovered in 1991 by Sumio Iijima, a researcher at NEC in Japan, and since then have been found to have enhanced physical and electronic properties compared to conventional carbon fibers and other materials. The diameter of individual carbon nanotubes, which may be single-wall or multi-wall structures, is typically in the range of single nanometers.

Only recently has technology been developed to form carbon nanotubes into microscale fibers (strands). The spinning of carbon nanotubes into microscale fibers is described in, for example, Lebovsky et al., U.S. Pat. No. 7,247,290, issued Jul. 24, 2007; Z. Zheng et al., U.S. Patent Application Publication No. 2007/0212290, published Sep. 13, 2007; and Z. Zheng et al., U.S. Patent Application Publication No. 2007/0116631, published May 24, 2007; and L. Zheng et al., *Adv. Mater.* 2007, 19, 2567-2570. The aforementioned publications are hereby incorporated by reference in their entirety. Such carbon nanotube fibers or strands may be obtained commercially from CNT Technologies (www.cnt-tech.com) and Nanocomp Technologies, Inc. (www.nanocomptech.com).

Preferably, each carbon nanotube strand employed in the woven fabric described herein is spun from a plurality of carbon nanotubes. The strands may be composed substantially entirely of carbon nanotubes or in part of carbon nanotubes. In the latter case, the strands may include, for example, a biocompatible polymer.

The present inventors have recognized that such carbon nanotube strands may be used advantageously in graft fabrics for medical devices. To perform its function in a blood vessel, a graft fabric must provide sufficient mechanical strength, wear resistance, and tear resistance. For example, due to blood flow through the vessel, implantable medical devices may experience pulsatile loading on the order of 400 million cycles over 10 years of in vivo use. Fatigue life is thus a critical consideration for device design. The challenge of producing graft fabrics with suitable properties increases with stent grafts intended for small entry points into the body or for implantation in small diameter vessels. Such stent grafts must be collapsible into a sufficiently low profile delivery configuration to fit within the intended delivery system while retaining all of the desired properties for their intended use.

The inventors believe that carbon nanotube strands are especially beneficial for preparing mechanically stable graft fabrics having a low delivery profile. Among the attributes of carbon nanotube strands are high tensile strength and toughness compared to other carbon fibers.

Referring to FIG. 1, it is preferred that the woven fabric 100 of the present disclosure includes a plurality of the carbon nanotube strands 110. According to a first embodiment, a first plurality 130 of the carbon nanotube strands 110 are aligned in a warp direction of the woven fabric, and a second plurality 140 of the carbon nanotube strands 110 are aligned in a weft direction of the woven fabric 100. The carbon nanotube strands 110 are interwoven with the textile strands 120, which are aligned in both the warp and weft directions of the woven fabric 100, according to this embodiment.

In the exemplary woven fabrics shown in FIGS. 1-4, the strands are woven in a plain weave characterized by a regular, one-to-one interlacing of strands. That is, each strand aligned in a first direction (e.g., warp direction) moves alternatively over and under adjacent strands aligned in a second direction (e.g., weft direction). This basic plain weave produces the maximum number of binding points (i.e., intersections of a single strand in the first direction with strands in the second direction), and is thus a firm, durable weave. However, the woven fabric may have any known weave, such as a basket weave, a rep or rib weave, a twill weave (e.g., straight twill, reverse twill, herringbone twill), a satin weave, or a double weave (e.g., double-width, tubular double weave, reversed double weave). FIGS. 5A-5D show examples of basket 500, rep 510, twill 520, and herringbone 530 weaves, respectively.

Figure 2:
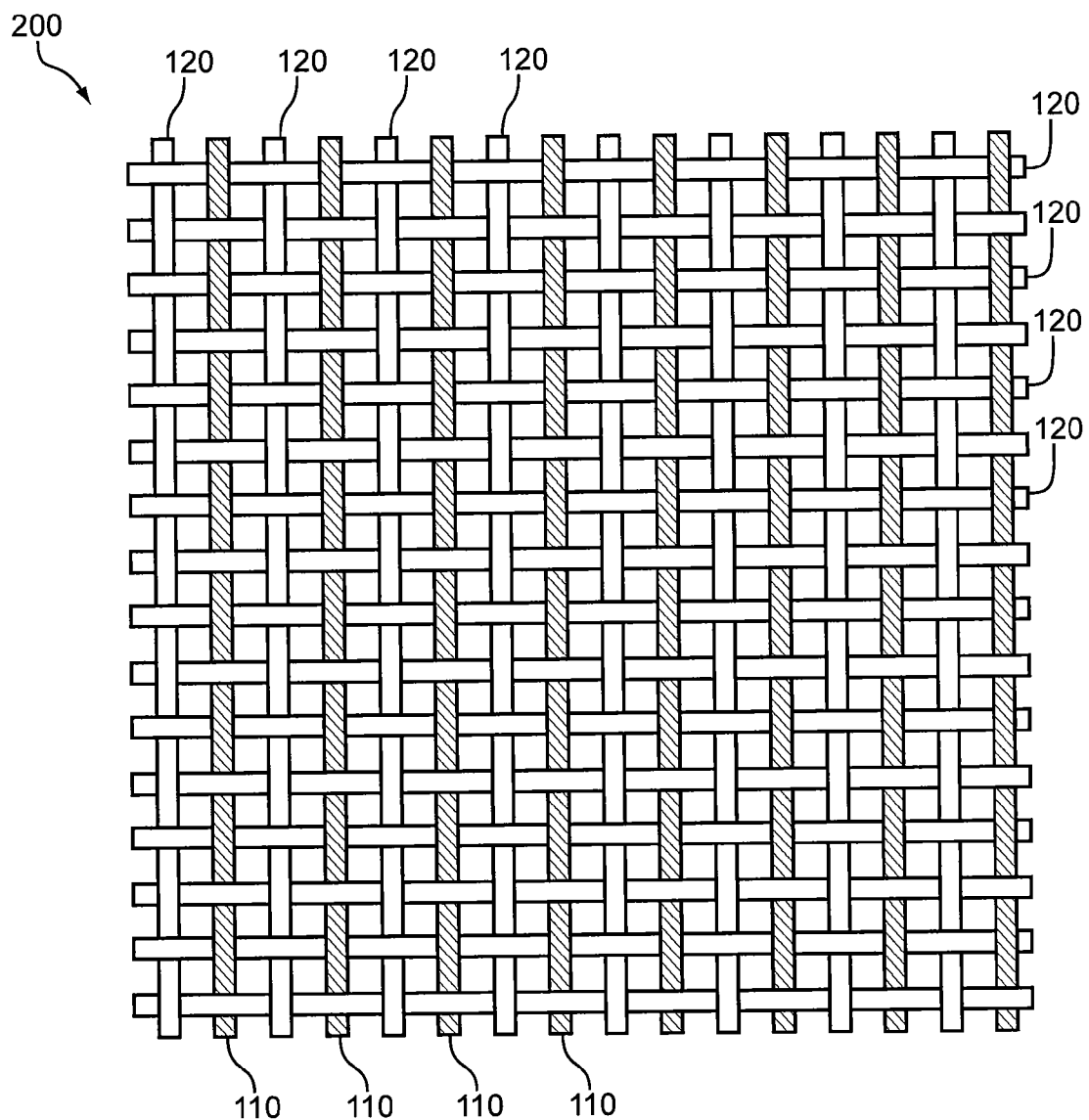
FIG. 2 is a schematic of a portion of a woven fabric including carbon nanotube strands and textile strands, according to another embodiment.

Referring to FIG. 2, which shows another embodiment of the woven fabric 200, all of the carbon nanotube strands 110 may be aligned in only one direction, either the warp direction or the weft direction, while the textile strands 120 are woven in both the warp and weft directions. It is preferable in this case that all of the carbon nanotube strands 110 are aligned in the weft direction, which is the generally the circumferential direction for a woven fabric used in a stent graft device.

Figure 3:
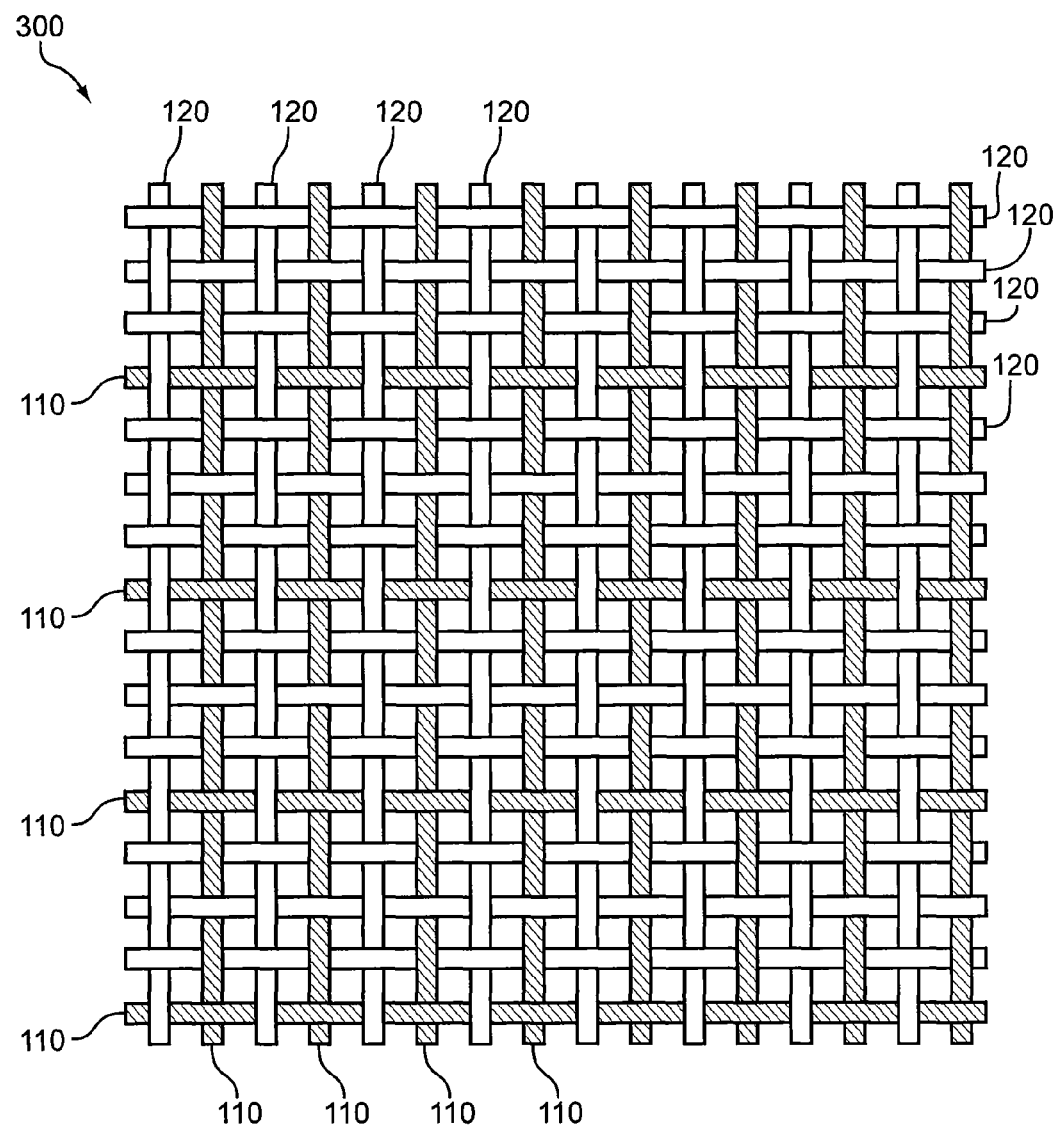
FIG. 3 is a schematic of a portion of a woven fabric including carbon nanotube strands and textile strands, according to another embodiment.

According to one embodiment, the woven fabric is composed primarily of textile strands with a smaller proportion of carbon nanotube strands. That is, less than 50% of the strands of the woven fabric may be carbon nanotube strands. The same proportion of nanotube strands may be woven in each direction, or each direction may include a different proportion of nanotube strands. For example, in each of the warp and weft directions there may be two textile strands for every carbon nanotube strand, such that 33% of the strands of the woven fabric are carbon nanotubes. Alternatively, in one direction of the woven fabric there may be one textile strand for every carbon nanotube strand, but in the other direction there may be two (or three, or more) textile strands for every carbon nanotube strand, such that 40% (or 33%, or less) of the strands of the woven fabric are carbon nanotubes. Other combinations of warp and weft direction proportions are also possible. Preferably, the weft direction has the higher density of carbon nanotube strands. A woven fabric 300 in which 33% of the strands thereof are carbon nanotube strands is illustrated in FIG. 3.

It is also envisioned that less than about 30% of the strands of the woven fabric may be carbon nanotube strands. For example, 25% of the strands may be carbon nanotube strands. Such a woven fabric may have three textile strands for every carbon nanotube strand in the each of the weft and warp directions, or one direction of the fabric may include two textile strands for every carbon nanotube strand, while the other direction includes four textile strands for every carbon nanotube strand. Other combinations of warp and weft direction proportions are also possible. Preferably, the weft direction has the higher density of carbon nanotube strands.

It is also contemplated that less than about 20%, or less than about 10%, or less than about 5% of the strands of the woven fabric may be carbon nanotube strands. A surprisingly small percentage of carbon nanotube strands may be effective in improving the strength and wear resistance of the woven fabric. As described above, the same proportion of nanotube strands may be woven in each direction, or each direction may include a different proportion of nanotube strands. For example, in a woven fabric in which 12.5% of the strands are carbon nanotube strands, seven textile strands may be woven in both the weft and warp directions for every carbon nanotube strand, or a different proportion may be woven in each direction, such as six textile strands for every carbon nanotube strand in one direction, and eight textile strands for every carbon nanotube strand in the other direction. In another example, a woven fabric having 10% carbon nanotube strands may include nine textile strands for every carbon nanotube strand in both the weft and warp directions, or a different proportion in each direction, such as seven textile strands for every carbon nanotube strand in one direction and eleven textile strands for every carbon nanotube strand in the other direction. Generally, it is preferred that the weft direction of the fabric has the higher proportion of carbon nanotube strands, since this direction is in greater need of reinforcement when the woven fabric is used in a stent graft.

Figure 4:
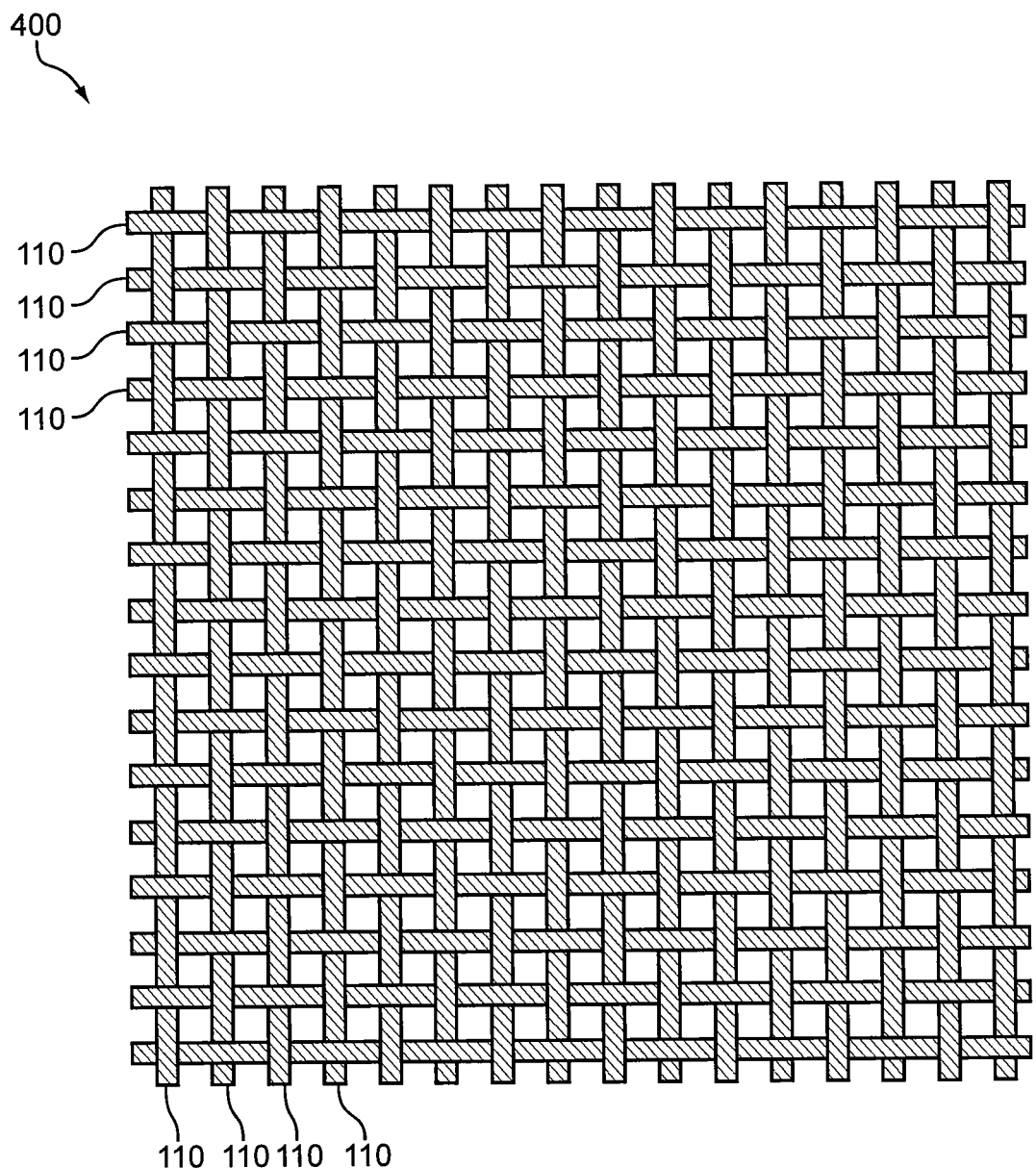
FIG. 4 is a schematic of a portion of a woven fabric including carbon nanotube strands, according to one embodiment.
Figure 5A:
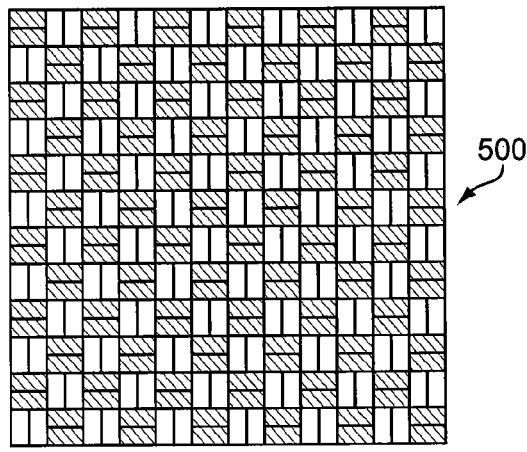
FIGS. 5A, 5B, 5C, and 5D are schematics of weave patterns of a woven fabric.
Figure 5B:
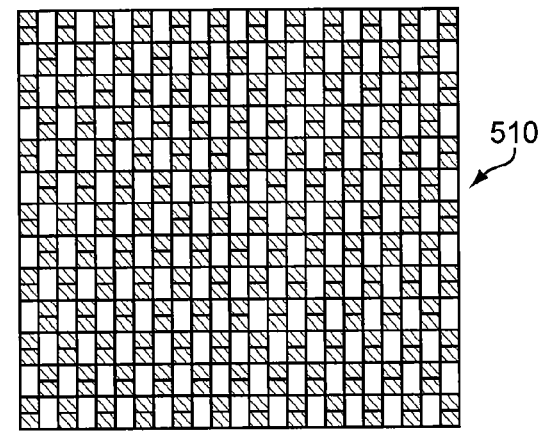
Figure 5C:
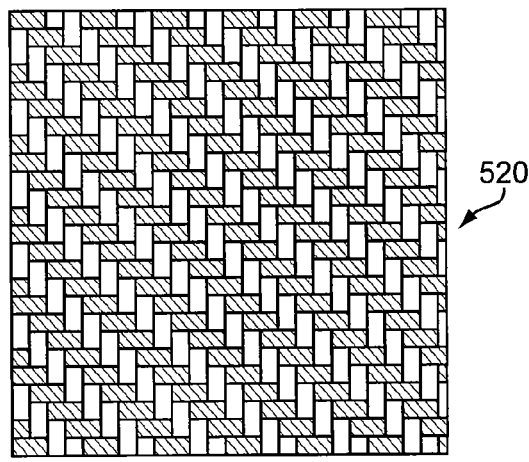
Figure 5D:
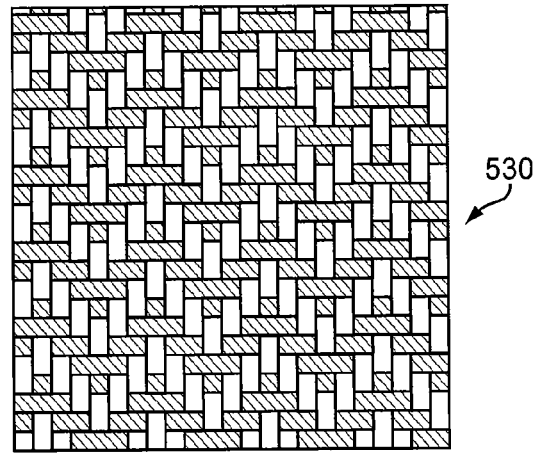

According to another embodiment, the woven fabric is composed primarily of carbon nanotube strands with a smaller proportion of textile strands. That is, at least about 50% of the strands of the woven fabric may be carbon nanotube strands. As described above, the same proportion of carbon nanotube strands may be woven in each direction, or each direction may include a different proportion of carbon nanotube strands. For example, a woven fabric in which 50% of the strands are carbon nanotube strands may include one textile strand for every carbon nanotube strand in both the weft and warp directions, as shown in FIG. 1, or, in another example, two textile strands may be woven for every carbon nanotube strand in one direction and one textile strand may be woven for every two carbon nanotube strands in the other direction. Other combinations of warp and weft direction proportions are also possible. Preferably, the weft direction of the fabric has the higher proportion of carbon nanotube strands. It is also envisioned that at least about 75% of the strands of the woven fabric may be carbon nanotube strands. According to another embodiment, all of the strands (100% of the strands) of the woven fabric are carbon nanotube strands, as shown in FIG. 4.

It may be advantageous for the textile strands of the woven fabric to have a denier smaller than that of textile strands employed in conventional woven fabrics. By using strands of a smaller denier, the thickness of the woven fabric may be reduced. The successful use of smaller denier textile strands in the woven fabric is facilitated by the exceptional tensile strength of the carbon nanotube strands. The denier of the textile strands may be in the range of from about 1 to about 100. Preferably, the denier of the textile strands is in the range of from about 1 to about 60. Even more preferably, the denier is in the range of from about 1 to about 40. For example, the denier of the textile strands may be about 10, about 20, about 30, or about 40.

The denier of the carbon nanotube strands is preferably less than that of the textile strands. According to one embodiment, the carbon nanotube strands have a denier of no more than about half the denier of the textile strands. For example, the carbon nanotube strands may have a denier in the range of from about 0.1 to about 50. Preferably, the carbon nanotube strands have a denier of from about 0.1 to about 30, or from about 0.1 to about 20. For example, the carbon nanotube strands may have a denier of about 0.1, about 1, about 10, or about 20.

Although denier is the preferred means of characterizing the size of strands employed in woven fabrics, it may also be useful to set forth preferred diameters of the carbon nanotube strands. To make a conversion from denier to diameter of the strand, the density in g/cm³ of the strand must be estimated or known, and the following equation may be employed:

$$\frac{\pi}{4} D^2 \cdot 9000 \text{ m} = \frac{d}{\rho \cdot \left(\frac{100 \text{ cm}}{\text{m}}\right)^3}$$

where d is denier, ρ is density, and D is the diameter of the strand in meters (which may be converted to microns by multiplying by $10^6$).

In the case of typical textile strands, specifically polyester strands, the density is approximately 1.3-1.5 g/cm³. Accordingly, by employing the preceding equation, it can be calculated that a 40 denier polyester fiber is approximately 64 microns in diameter. For the purposes of carrying out the same calculation for carbon nanotube strands, the density of the carbon nanotube strands is taken to be the density of graphite, which is approximately 1.9-2.3 g/cm³. Accordingly, it can be calculated that carbon nanotube strands having a denier of 20 have a diameter of about 37 microns. Similarly, it can be calculated that carbon nanotube strands having a denier of 0.1 have a diameter of about 3 microns. Thus, the carbon nanotube strands employed in the woven fabric may have a diameter in the range of from about 3 microns to about 37 microns, according to a preferred embodiment.

The spacing of the strands within the weave is expressed in terms of a linear density or line density of strands, and may depend on the denier of the strands. A higher linear density is indicative of a smaller spacing between adjacent strands. For a 40 denier textile strand, a line density of about 250 ends per inch is preferred in the warp direction, which generally corresponds to the longitudinal direction in the case of a woven fabric for a stent graft. In the weft direction, which generally corresponds to the circumferential direction in the case of a woven fabric for a stent graft, a line density of about 150 picks per inch is preferred. The line density in the weft direction is preferably in the range of from about 100 picks per inch to about 200 picks per inch, and the line density in the warp direction is preferably in the range of from about 200 ends per inch to about 300 ends per inch, depending on the denier of the strands.

The woven fabric preferably has a thickness that is reduced compared to conventional graft fabrics. A thickness reduction may be achieved by the use of smaller denier strands and/or by a reduced density of the weave. As discussed above, the enhanced strength of the carbon nanotube strands may facilitate this reduction in thickness. According to one embodiment, the thickness of the woven fabric is about 0.25 mm or less. More preferably, the thickness is about 0.125 mm or less. Even more preferably, the thickness of the woven fabric is about 0.08 mm or less, such as about 0.05 mm.

At reduced thicknesses, the woven fabric may have an increased permeability, that is, an increased susceptibility to fluid leakage (e.g., blood leakage). In order to compensate for this increased permeability, according to one embodiment, the woven fabric may be coated with a polymer such as, for example, a siloxane, polyurethane, polycarbonate urethane, or PTFE. The coating may have a thickness of about 0.02 mm or less, according to a preferred embodiment. The coating may be applied by dipping, spraying, or any other means of applying a solution containing the polymer and a suitable solvent to the woven fabric. The solvent is evaporated and the polymer is then cured, if a curable polymer such as silicone is used. Alternatively, the coating may be formed by impregnating the woven fabric with the polymer.

The textile strands may be made of any natural or synthetic material. Preferably, the material is biocompatible. For example, biocompatible materials from which textile strands may be formed include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be suitable for use as textile strands if they can be rendered biocompatible. For example, surface modification techniques may be employed to impart biocompatibility to such materials. Examples of surface modification techniques include graft polymerization of biocompatible polymers from the material surface, coating of the surface with a crosslinked biocompatible polymer, chemical modification with biocompatible functional groups, and immobilization of a compatibilizing agent such as heparin or other substances.

Polymers that can be formed into fibers for making textile strands are preferred. For example, suitable polymers include polyethylene, polypropylene, polyaramids, polyacrylonitrile, nylons and cellulose, in addition to polyesters, fluorinated polymers, and polyurethanes as listed above. Desirably, the textile strands comprise biocompatible polyesters. For example, the textile strands may comprise polyethylene terephthalate and PTFE. A preferred commercial example of polyethylene terephthalate especially suited for weaving is Dacron®. These materials have good physical characteristics and are generally inexpensive, easy to handle, and suitable for clinical application.

It is also preferred that the carbon nanotube strands are biocompatible, or capable of being rendered biocompatible by a surface treatment, coating or the like. A biocompatible material is substantially non-toxic in the in vivo environment of its intended use, and is not substantially rejected by the patient's physiological system. The biocompatibility of a material can be gauged using the tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

According to one embodiment, the carbon nanotube strands may be functionalized for the attachment of drug molecules, proteins, peptides, genes or other biological molecules so as to impart a drug eluting function to the woven fabric. Such biological molecules, which may be generally referred to as "pharmaceutical agents," may be bound to sidewalls or surfaces of the carbon nanotubes that make up the carbon nanotube strands. The functionalization may be carried out prior to or after forming the strands. For example, a pharmaceutical agent such as paclitaxel may be bound to or otherwise incorporated into the carbon nanotube strands for the purpose of treating restenosis or other endoluminal conditions. Preferably, the pharmaceutical agent can be controllably released from the carbon nanotube strands of the woven fabric at an appropriate time or over a desired duration of time.

The woven fabric may include an extracellular matrix material (ECM), such as submucosa, incorporated therein or thereon to enhance the biofixation characteristics of stent grafts or other implantable devices that include the fabric. Biofixation, or biologically attaching the device to the vessel wall through tissue growth into and around the device, can help to address the problem of stent graft migration within the vessel due to hemodynamic forces. Stent graft migration may lead to endoleaks, a leaking of blood into the aneurysm sac between the outer surface of the graft and the inner lumen of the blood vessel that can increase the risk of vessel rupture. Biofixation may be effected by endothelialization as well as the proliferation of fibroblasts, smooth muscle cells and the growth of connective tissue matrices. A preferred type of submucosa for the promotion of biofixation is derived from the intestines, for example the small intestine, of a warm blooded vertebrate; i.e., small intestine submucosa (SIS). SIS is commercially available from Cook Biotech, West Lafayette, Ind.

According to one embodiment, the woven fabric may be impregnated or coated with SIS or another ECM. Preferably, the SIS or other ECM is processed into a filament, thread or strand suitable for weaving into the fabric. A plurality of ECM strands may be interwoven with the textile strands and/or carbon nanotube strands of the woven fabric to promote biofixation of an implantable device including the fabric.

The woven fabric may further include at least one bioabsorbable strand interwoven with the textile and/or carbon nanotube strands. Bioabsorbable strands degrade over time and are absorbed by the body, eliminating the need for removal. Preferably, the bioabsorbable strand is made of a bioabsorbable polymer, such as, for example, polylactic acid (PLA), polyglycol acid (PGA), polyglactin (polyglycol acid-polylactic acid copolymer), polydioxanone, polyglyconate (trimethylene carbonate-glycolide copolymer), or a copolymer of ε-caprolactone with polyglycol acid or polylactic acid. According to one embodiment, the woven fabric includes a plurality of bioabsorbable strands interwoven with the textile strands and/or the carbon nanotube strands.

The woven fabric may also include at least one metallic wire interwoven with the textile and/or carbon nanotube strands. The metallic wire may provide structural support to the graft, thereby eliminating the need for a stent structure, or it may have another function, such as imparting superelastic characteristics or radiopacity to the graft fabric. The metallic wire is preferably formed of a biocompatible metal or alloy. Appropriate metals and alloys may include, for example, stainless steel, nickel-titanium (e.g., Nitinol), gold, platinum, palladium, titanium, tantalum, tungsten, molybdenum, or alloys thereof. Other suitable alloys may include cobalt-chromium alloys such as L-605, MP35N, and Elgiloy; nickel-chromium alloys, such as alloy 625; and niobium alloys, such as Nb-1% Zr, and others.

According to one embodiment, the metal or alloy of the metallic wire may have shape memory/superelastic characteristics that enable the wire to "remember" and recover a previous shape. In the case of nickel-titanium shape memory alloys, the source of the shape recovery is a phase transformation between a lower temperature phase (martensite) and a higher temperature phase (austenite), which may be driven by a change in temperature (shape memory effect) or by the removal of an applied stress (superelastic effect). Strain introduced into the alloy in the martensitic phase to achieve a shape change may be substantially recovered upon completion of a reverse phase transformation to austenite, allowing the alloy to return to the previous shape. Recoverable strains of up to about 8-10% are generally achievable with nickel-titanium shape memory alloys. Other suitable shape memory alloys for the metallic wire may include, for example, Cu—Zn—Al alloys and Fe—Ni—Al alloys.

The woven fabric described herein is suitable for use in a variety of implantable or insertable medical devices. The medical device may be any device comprising a woven fabric that is introduced temporarily or permanently into the body for the treatment of a medical condition. For example, such medical devices may include, but are not limited to: endovascular grafts, vascular grafts, stent grafts, balloon catheters, meshes, filters (e.g., vena cava filters), tissue scaffolds, myocardial plugs, valves (e.g., venous valves), pelvic implants, various types of dressings, or other known biocompatible devices. The medical device may be a bifurcated integrated stent-graft, an integrated stent-graft configured for any blood vessel including coronary arteries and peripheral arteries (e.g., renal, superficial femoral, carotid, and the like), a urethral integrated stent-graft, a biliary integrated stent-graft, a tracheal integrated stent-graft, a gastrointestinal integrated stent-graft, or an esophageal integrated stent-graft, for example.

Figure 6:
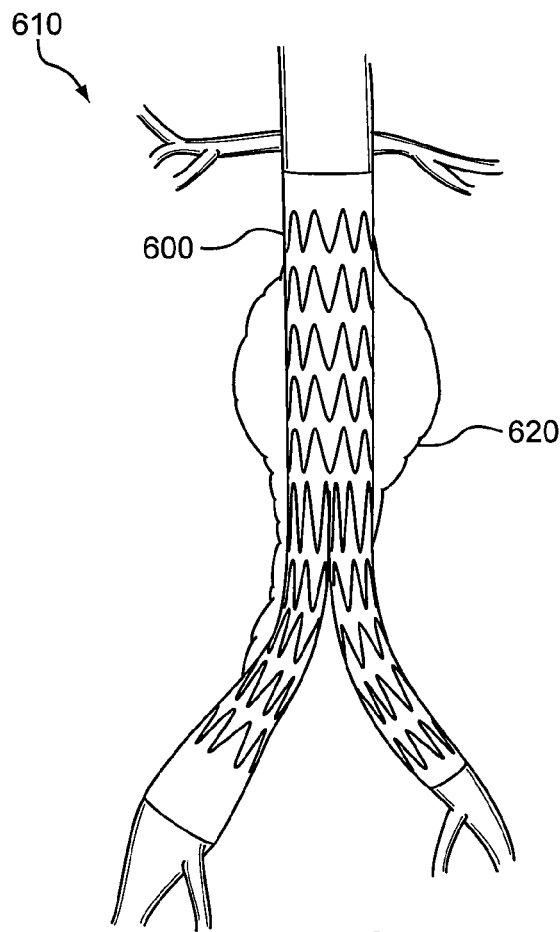
FIG. 6 is an illustration of an endovascular graft deployed at a site of an aneurysm.

Also described herein is an implantable medical device comprising a component and a woven fabric secured to the component. The woven fabric includes a plurality of woven carbon nanotube strands, and each of the carbon nanotube strands comprises a plurality of carbon nanotubes. FIG. 6 depicts an exemplary endovascular graft 610 comprising an exemplary woven fabric 600. The endovascular graft 610 is shown in a deployed configuration at the site of an aneurysm 620.

Figure 7:
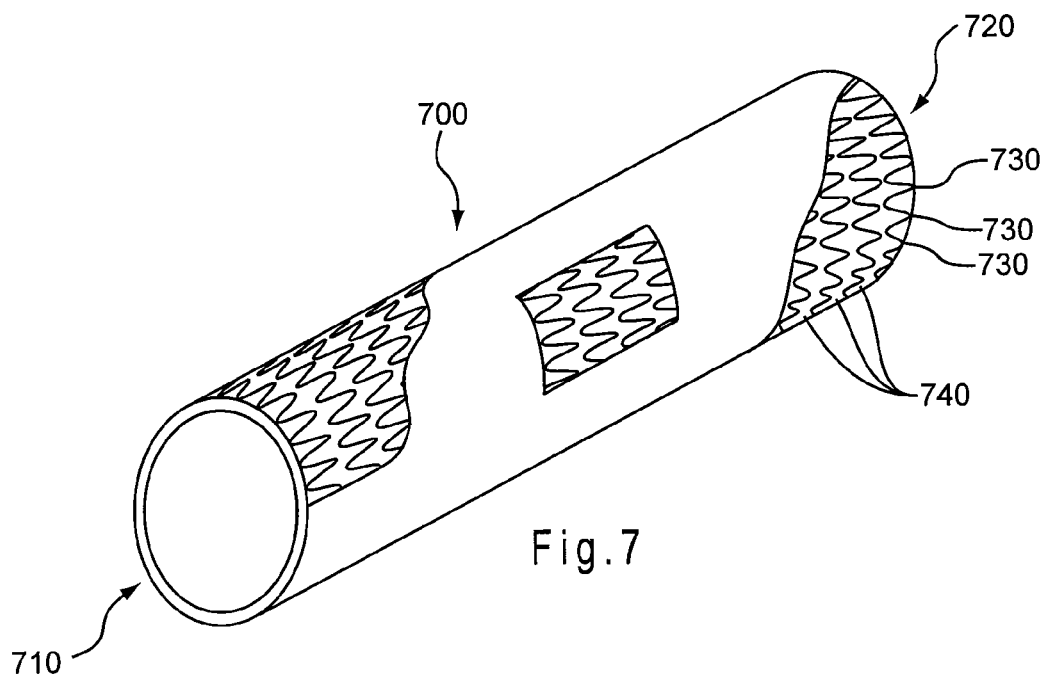
FIG. 7 is a schematic of a portion of a stent graft including a woven fabric, according to one embodiment.

FIG. 7 is a schematic of a stent graft 700 having a tubular stent structure 710 and a woven fabric 720 including a plurality of woven carbon nanotube strands. The woven fabric 720 has longitudinal strands 730 and circumferential strands

740, although the strands may have any desired orientation with respect to the stent structure 710. The longitudinal strands 730 and circumferential strands 740 may have any suitable weave configuration, such as those shown in FIGS. 1-4 and 5A-5D. Although only two-dimensional weave patterns are shown, it possible for the woven fabric 720 to have strands (e.g., carbon nanotube strands) woven in a third direction.

According to one embodiment, substantially all of the longitudinal and circumferential strands 730, 740 are carbon nanotube strands. According to another embodiment, the longitudinal and circumferential strands 730, 740 comprise carbon nanotube strands interwoven with textile strands.

According to yet another embodiment, the longitudinal and circumferential strands comprise carbon nanotube strands interwoven with textile strands and with one or more additional woven strands. For example, the circumferential strands 740 may comprise textile strands and carbon nanotube strands, and the longitudinal strands 730 may comprise textile strands, carbon nanotube strands, and SIS strands. In another example, circumferential strands 740 of the woven fabric 720 may comprise textile strands, carbon nanotube strands, and metallic wire strands, and the longitudinal strands 730 may comprise textile strands and carbon nanotube strands. Other combinations of the above-described strands are also possible. The description of the carbon nanotube strands and the textile strands set forth previously (e.g., proportion of strands, denier sizes, etc.), although not repeated here, may be assumed to be applicable to the woven fabric 720 shown schematically in FIG. 7.

Weaving methods known in the art may be employed to produce the woven fabric described herein according to various embodiments. For example, the fabric may be woven on a table loom, a floor loom, a jacquard loom, a counterbalance loom, a jack loom, or an upright loom. Desirably, the fabric is woven on a floor loom.

A woven fabric for an implantable medical device, and an implantable medical device including such a woven fabric, have been described. The inventors believe that by weaving carbon nanotube strands into a fabric, they can produce a woven fabric having a reduced thickness without sacrificing strength or wear resistance. An implantable medical device, such as a stent graft, including this woven fabric may have the advantage of better packability into lower profile delivery systems than existing devices.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A woven fabric for an implantable medical device, the woven fabric comprising a plurality of carbon nanotube strands interwoven with a plurality of textile strands, wherein each of the carbon nanotube strands comprises a plurality of carbon nanotubes and has a denier of from about 0.1 to about 50, and wherein the carbon nanotube strands comprise less than about 50% of a total number of strands of the woven fabric.

2. The woven fabric of claim 1, wherein each of the carbon nanotube strands is spun from the plurality of carbon nanotubes.

3. The woven fabric of claim 1, wherein a first plurality of the carbon nanotube strands are aligned in a warp direction and a second plurality of the carbon nanotube strands are aligned in a weft direction.

4. The woven fabric of claim 1, wherein the carbon nanotube strands comprise less than about 30% of a total number of strands of the woven fabric.

5. The woven fabric of claim 1 having a thickness of about 0.125 mm or less.

6. The woven fabric of claim 1, wherein a line density in a weft direction of the woven fabric ranges from about 100 picks per inch to about 200 picks per inch, and wherein a line density in a warp direction ranges from about 200 ends per inch to about 300 ends per inch.

7. The woven fabric of claim 1, wherein the textile strands comprise a denier of from about 1 to about 60.

8. The woven fabric of claim 1, wherein the carbon nanotube strands comprise a denier of from about 0.1 to about 30.

9. The woven fabric of claim 1, wherein the carbon nanotube strands comprise a denier of no more than about half that of the textile strands.

10. The woven fabric of claim 1, wherein the textile strands comprise a polymer.

11. The woven fabric of claim 1, further comprising one or more pharmaceutical agents releasably attached to the carbon nanotube strands, thereby imparting a drug eluting capability to the woven fabric.

12. The woven fabric of claim 1, further comprising strands of an extracellular matrix material woven into the fabric.

13. The woven fabric of claim 1, further comprising bioabsorbable polymeric strands woven into the fabric.

14. The woven fabric of claim 1, further comprising at least one metallic wire woven into the fabric.

15. The woven fabric of claim 1, wherein the woven fabric comprises a weave selected from the group consisting of a plain weave, a basket weave, a twill weave, a rep weave, and a herringbone weave.

16. The woven fabric of claim 1, wherein a first plurality of the carbon nanotube strands are aligned in a warp direction and a second plurality of the carbon nanotube strands are aligned in a weft direction, the carbon nanotube strands comprising less than about 50% of a total number of strands of the woven fabric, and wherein each of the carbon nanotube strands is spun from the plurality of carbon nanotubes, and
    wherein the textile strands comprise polyester strands having a denier of from about 1 to about 60, and wherein the carbon nanotube strands comprise a denier of no more than about half that of the polyester strands, and
    wherein the woven fabric has a thickness of about 0.125 mm or less.

17. An implantable medical device comprising:
    a component;
    a fabric secured to the component, the fabric comprising a plurality of textile strands interwoven with a plurality of woven carbon nanotube strands, wherein each of the carbon nanotube strands comprises a plurality of carbon nanotubes and has a denier of from about 0.1 to about 50, and wherein the carbon nanotube strands comprise less than about 50% of a total number of strands of the woven fabric.

18. The implantable medical device of claim 17, wherein the component is a stent.

* * * * *